United States Patent
Dickinson et al.

(10) Patent No.: US 8,264,127 B2
(45) Date of Patent: Sep. 11, 2012

(54) LOW FREQUENCY ACOUSTIC TRANSDUCER FOR A PROBE FOR NON-DESTRUCTIVE TESTING

(75) Inventors: Laurence Dickinson, Epping (AU); Graeme Edwards, Berowra (AU); Adam Batten, Bella Vista (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 488 days.

(21) Appl. No.: 12/223,874

(22) PCT Filed: Feb. 12, 2007

(86) PCT No.: PCT/AU2007/000139
§ 371 (c)(1),
(2), (4) Date: Mar. 12, 2010

(87) PCT Pub. No.: WO2007/092991
PCT Pub. Date: Aug. 23, 2007

(65) Prior Publication Data
US 2010/0187951 A1    Jul. 29, 2010

(30) Foreign Application Priority Data
Feb. 13, 2006 (AU) ............... 2006900683

(51) Int. Cl.
*B06B 1/06* (2006.01)
(52) U.S. Cl. ............. 310/336; 310/331; 310/354
(58) Field of Classification Search ............. 310/336, 310/330, 331, 354
See application file for complete search history.

(56) References Cited

U.S. PATENT DOCUMENTS

| | | | |
|---|---|---|---|
| 3,140,859 A | 7/1964 | Scarpa | |
| 4,286,470 A * | 9/1981 | Lynnworth | 73/861.18 |
| 4,641,054 A | 2/1987 | Takahata et al. | |
| 5,189,915 A | 3/1993 | Reinhart et al. | |

(Continued)

FOREIGN PATENT DOCUMENTS

| | | |
|---|---|---|
| DE | 35 25 724 | 2/1986 |
| FR | 2 835 981 | 8/2003 |
| WO | 03/069779 | 8/2003 |

OTHER PUBLICATIONS

International Search Report for PCT/AU2007/000139, mailed Apr. 2, 2007.

*Primary Examiner* — Walter Benson
*Assistant Examiner* — Bryan Gordon
(74) *Attorney, Agent, or Firm* — Nixon & Vanderhye P.C.

(57) ABSTRACT

The present invention provides a low frequency acoustic transducer for non-destructive testing of a test structure. The transducer is arranged for conversion between electrical energy and acoustic energy associated with an acoustic wave propagating through a portion of the test structure. The transducer comprises a bending actuator for generating the acoustic wave by generating a vibration from an electrical signal or for generating an electrical signal from a vibration generated by the received acoustic wave. The bending actuator has a vibration surface and a contact area surrounded by a portion of the vibration surface. The transducer further comprises a mode setting member that has a rigid portion which is in direct mechanical contact with the bending actuator at the contact area such that, within the contact area, an amplitude of the vibration is substantially suppressed. The location and shape of the contact area determine a bending mode associated with a resonance frequency of the bending actuator.

29 Claims, 5 Drawing Sheets

U.S. PATENT DOCUMENTS

| | | |
|---|---|---|
| 6,504,289 B2 * | 1/2003 | Toda et al. .................. 310/334 |
| 6,739,575 B2 * | 5/2004 | Cotton et al. ............ 251/129.06 |
| 2003/0024316 A1 * | 2/2003 | Han et al. ........................ 73/629 |
| 2005/0162040 A1 | 7/2005 | Robert |
| 2005/0236934 A1 * | 10/2005 | Koganezawa et al. ........ 310/328 |
| 2006/0001334 A1 * | 1/2006 | Shiba .............................. 310/325 |
| 2006/0055399 A1 * | 3/2006 | Georgeson et al. ........... 324/232 |
| 2006/0129204 A1 * | 6/2006 | Pless et al. ....................... 607/45 |
| 2008/0060195 A1 * | 3/2008 | Straub et al. .................... 29/854 |

* cited by examiner

LOW FREQUENCY ACOUSTIC TRANSDUCER FOR A PROBE FOR NON-DESTRUCTIVE TESTING

This application is the U.S. national phase of International Application No. PCT/AU2007/000139, filed 12 Feb. 2007, which designated the U.S. and claims priority to Australia Application No. 2006900683, filed 13 Feb. 2006, the entire contents of each of which are hereby incorporated by reference.

FIELD OF THE INVENTION

The present invention broadly relates to a low frequency acoustic transducer for a probe for non-destructive testing of a test structure.

BACKGROUND OF THE INVENTION

Ultrasonic vibrations for testing a structure have been used for many years in the field of Non-Destructive Testing (NDT).

Available ultrasonic vibration probes usually operate in the ultrasonic frequency range of 100 kHz to 10 MHz or higher. However, some materials do not respond well to such high frequency excitations and the use of lower frequency vibrations is advantageous. Application areas for low frequency NDT include advanced lightweight laminates and composite sandwich panels typically found in aerospace and marine structures.

The most popular low frequency technique is the so-called "Pitch-Catch" technique, where a probe comprises two identical transducers with one transducer set as a dedicated transmitter (pitcher) and the another transducer as a dedicated receiver (catcher). Such a "Pitch-Catch" NDT system can detect the mechanical response of a test structure and comparing this response to a response of a known reference item provides information concerning possible damage of the test structure.

A Pitch-Catch transducer may include a circular Lead-Zirconate-Titanate (PZT) bending actuator held either at its edges, or sandwiched between a compliant material such as a pair of rubber O-rings. The PZT elements are coupled to a test structure through a thick pin held in place with O-rings, or a rubber or cork sleeve so that the pin may be replaced when worn. Although manufacturers of these transducers are often quoting a usable frequency range of up to 70 kHz, inherent resonant artefacts within the designs are usually present and can interfere with measurements within the stated frequency range. Further, the designs of these transducers are often asymmetrical with electrical contact wires soldered to the disc. Asymmetry can contribute to degrading of the harmonic response of the transducer.

A low frequency NDT probe should ideally be used in a region of linear response away from any resonant artefacts of the probe. However, resonant artefacts between 20 and 30 kHz of known Pitch-Catch probes limit their linear frequency range to approximately 15 kHz. For many applications this limitation is of disadvantage and consequently there is a need for technological advancement.

SUMMARY OF THE INVENTION

The present invention provides in a first aspect a low frequency acoustic transducer for a probe for non-destructive testing of a test structure, the transducer being arranged for conversion between electrical energy and acoustic energy associated with an acoustic wave that propagated or will propagate through a portion of the test structure, and comprising:

a bending actuator for generating an acoustic wave by generating a vibration from an electrical signal or for generating an electrical signal from a vibration generated by a received acoustic wave, the bending actuator having a vibration surface and a contact area surrounded by a portion of the vibration surface, and a mode setting member having a rigid portion which is in direct mechanical contact with the bending actuator at the contact area such that, within the contact area, an amplitude of the vibration is substantially suppressed, wherein the location and shape of the contact area determine a bending mode associated with a resonance frequency of the bending actuator.

The mode setting member typically supports the bending actuator and the bending actuator typically is only supported by the mode setting member.

At least some artificial bending modes typically are substantially suppressed by the mode setting member. For example, the transducer typically is arranged so that artificial resonances having a frequency within a range of 100 Hz, 1 kHz or 2 kHz to 10, 15, 20, 28, 30, 35, 40, or 50 kHz are substantially suppressed which results in a wide frequency range that is largely free of any resonances.

The mode setting member may be arranged so that the bending actuator is contacted at a contact area having any suitable shape and encouraging any possible bending mode, but typically is arranged so that a natural fundamental bending mode, which the bending actuator would also have without the mode setting member, is unsuppressed.

The vibration surface typically comprises opposite first and second side portions of the bending actuator. The mode setting member typically comprises a first mode setting clamping member positioned at the first side portion of the bending actuator and a second mode setting clamping member positioned at the second side portion of the bending actuator so that the bending actuator is clamped between the mode setting members.

The first and second mode setting clamping members may have any suitable shape, but typically are shaped to clamp the bending actuator at opposite positions along a closed line on the first and second sides of the bending actuator. For example, the mode setting clamping members may each have a ring-like continuous clamping surface which clamps the bending actuator or may be arranged for clamping at points or separated areas along the line. The mode setting clamping members may have a ring-like clamping surface that has a tapered cross-sectional profile having a clamping edge which may be sharp or rounded. The clamping surface typically is circular and the bending actuator typically also has a circular disc-like shape.

In one specific embodiment of the present invention the bending actuator comprises a disc of a bimorph material, which typically comprises at least two layers of PZT having opposing electrical polarisations, and may have a diameter of approximately 6 to 15 mm and a thickness of approximately 0.3 to 1 mm.

Each mode setting clamping member may also be rigidly connected, for example by soldering, with an electronic component or a circuit board such as a printed circuit board. The circuit board or the electronic component may include an amplifier such as a preamplifier.

The first and the second mode setting clamping members typically are electrically conductive members and provide electrical connections for the bending actuator. Separate electrical contacts, such as those which are soldered onto the bending actuator, usually load the bending actuator asymmetrically and affect the resonance properties. If the mode setting clamping members themselves provide the electrical contacts, such separate electrical contacts can be avoided which is of significant advantage.

The bending actuator typically comprises a piezoelectric material such as a material having a Perovkite structure (eg Lead Zirconium Titanate, PZT) and typically is a bimorph bending actuator.

The transducer typically comprises a coupling pin, such as a cylindrical pin, which is glued or otherwise rigidly attached to the bending actuator. Alternatively, the bending actuator may be integrally formed with the coupling pin from the same material. The coupling pin typically is positioned and shaped so that the coupling pin does not result in an additional bending or compressional mode associated with a frequency that is below that of the natural bending mode of the bending actuator. The coupling pin may be arranged for direct contact with the test structure or may comprise a further pin for contacting the test structure and which typically can be exchanged. However, the transducer typically is arranged so that the pin, attached to the bending actuator or formed with the bending actuator, does not contact any other portion of the transducer or the probe.

The coupling pin may be composed of one material or may comprise two or more materials selected for balancing acoustic matching and harmonic response. For example, the coupling pin may comprise a plastics or ceramics material. Alternatively, the coupling pin may comprise a metallic material such as stainless steel or titanium.

Further, the coupling pin may be coupled to an element for reducing friction with the test structure and may comprise a bearing, such as a ball bearing, or a coating which allows gliding of the coupling pin over the test structure with relatively low friction. A hardwearing coating, such as titanium nitride coating, may also be used to increase the wear resistance of the pin. The element for reducing friction may also be a sheet of a material formed from a flexible material that is attached to a housing of the probe and through which the coupling pin establishes contact with the test structure.

The transducer typically also comprises a stiffening element at a bottom portion of the bending actuator and around the coupling pin. The stiffening element further increases the resonance frequency by providing additional stiffness. The stiffening element may be shaped and may be coupled to the mode setting member so that the stiffening element promotes self-alignment of the mode setting member and the bending actuator relative to each other. The transducer may also comprise a similar stiffening element at a top portion of the bending actuator.

The stiffening element typically has a diameter which is between 0.25 and 0.9 of that of the bending actuator, and in one specific embodiment the stiffening element has approximately the same diameter as the circular contact area of the mode setting clamping members. The thickness of the stiffening element typically is of the order of 0.1 to 1.0 mm. The stiffening element may be composed of any suitable material, but typically is formed from a plastics material. The coupling pin and the stiffening element may be composed of the same material and may also be integrally formed from the same material.

The transducer typically comprises a housing having a spring loaded mechanism which effects the clamping of the bending actuator between the mode setting clamping members.

The transducer may operate as an emitter of an acoustic wave. In this case an electrical ac voltage typically is applied to the bending actuator to generate the vibration.

Alternatively or additionally, the transducer may operate as a receiver of an acoustic wave. In this case the received acoustic wave generates the vibration of the bending actuator which generates an electrical ac voltage.

The present invention provides in a second aspect a low frequency acoustic transducer for a probe for non-destructive testing of a test structure, the transducer being arranged for conversion between electrical energy and acoustic energy associated with an acoustic wave that propagated or will propagate through a portion of the test structure, and comprising:

a bending actuator for generating an acoustic wave by generating a vibration from an electrical signal or for generating an electrical signal from a vibration generated by a received acoustic wave, the bending actuator having opposite first and second surfaces, a first contact member contacting the first side portion of the bending actuator, and a second contact member contacting the second side portion of the bending actuator, wherein the first and second contact members clamp the bending actuator and provide electrical contacts for the bending actuator.

The present invention provides in a third aspect a probe for non-destructive testing comprising the above-described transducer according to the first or second aspect of the present invention.

In one specific embodiment of the third aspect of the present invention the transducer is one of at least two transducers. In this case at least one transducer of the probe typically is arranged for generating the acoustic wave and at least one other transducer of the probe is arranged for receiving a return signal from the test structure. For example, the probe may comprise an array of the transducers. The function of the transducers may also be reversible, for example in a periodical manner, which enables obtaining differential data.

In another specific embodiment of the third aspect of the present invention the probe is arranged for generating the acoustic wave and receiving a return signal by the same transducer. In this case the probe typically is arranged for measurement of an electrical impedance of the transducer during testing of a test structure from which a response signal can be derived.

The present invention provides in a fourth aspect a method of generating an acoustic wave for non-destructive testing of a test structure, the method comprising:

applying an ac electrical signal to a bending actuator for generating a vibration, the vibration generating an acoustic wave for propagation through a portion of the test structure, the bending actuator having a vibration surface and a contact area surrounded by a portion of the vibration surface, and contacting the bending actuator by a rigid portion of a mode setting member at the contact area such that, at the contact area, an amplitude of the vibration is substantially suppressed, wherein the location and shape of the contact area determine a bending mode associated with a resonance frequency of the bending actuator.

The step of contacting the bending actuator typically comprises clamping the bending actuator between mode setting clamping members at a ring-like area of the bending actuator.

The method may also comprise the additional step of controlling a resonance frequency of the bending actuator by applying a dc voltage or selected additional ac voltage across at least a portion of the bending actuator.

The present invention provides in a fifth aspect a method of receiving an acoustic wave for non-destructive testing of a test structure, the method comprising:

exposing a bending actuator to the acoustic wave received from the test structure whereby a vibration and an associated ac voltage is generated, the bending actuator having a vibration surface and a contact area surrounded by a portion of the vibration surface, and contacting the bending actuator by a rigid portion of a mode setting member at the contact area such that, at the contact area, an amplitude of the vibration is substantially suppressed, wherein the location and shape of the contact area determine a bending mode associated with a resonance frequency of the bending actuator.

The step of contacting the vibration surface typically comprises clamping the bending actuator between mode setting clamping members at a ring-like area of the bending actuator.

The invention will be more fully understood from the following description of specific embodiments of the invention. The description is provided with reference to the accompanying drawings.

DETAILED DESCRIPTION OF SPECIFIC EMBODIMENTS

Figure 1:
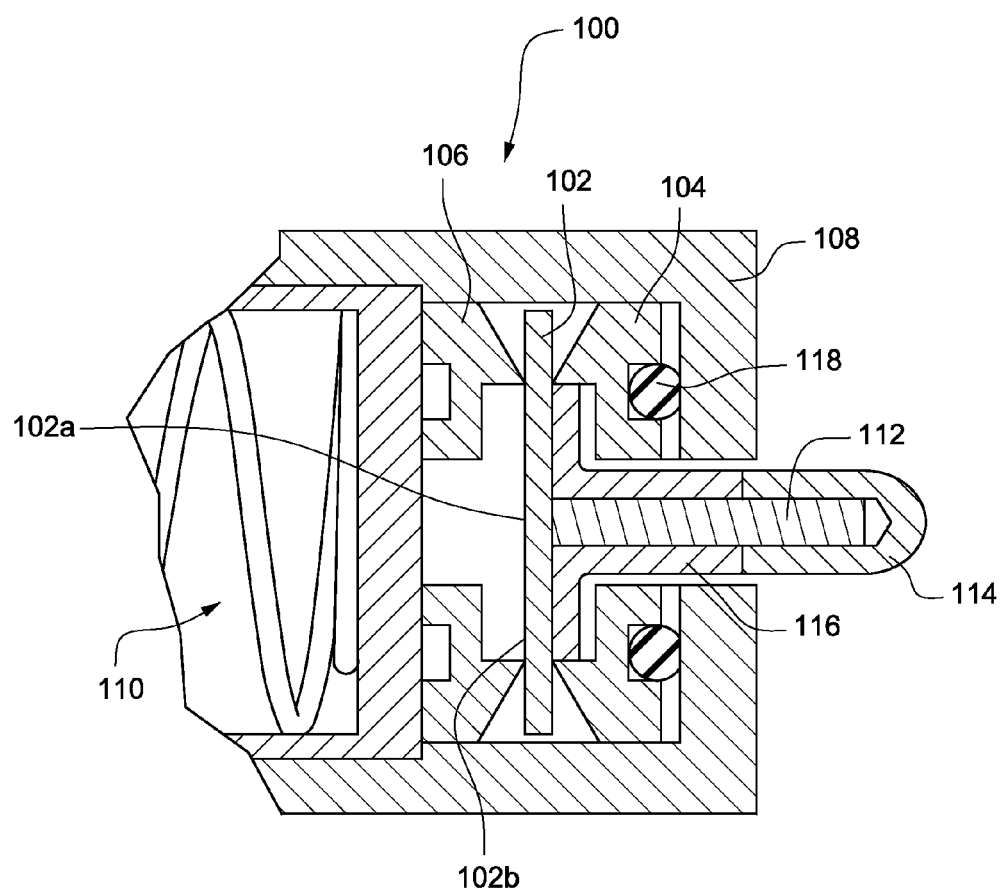
FIG. 1 shows a cross-sectional representation of a transducer according to an embodiment of the present invention.
Figure 2:
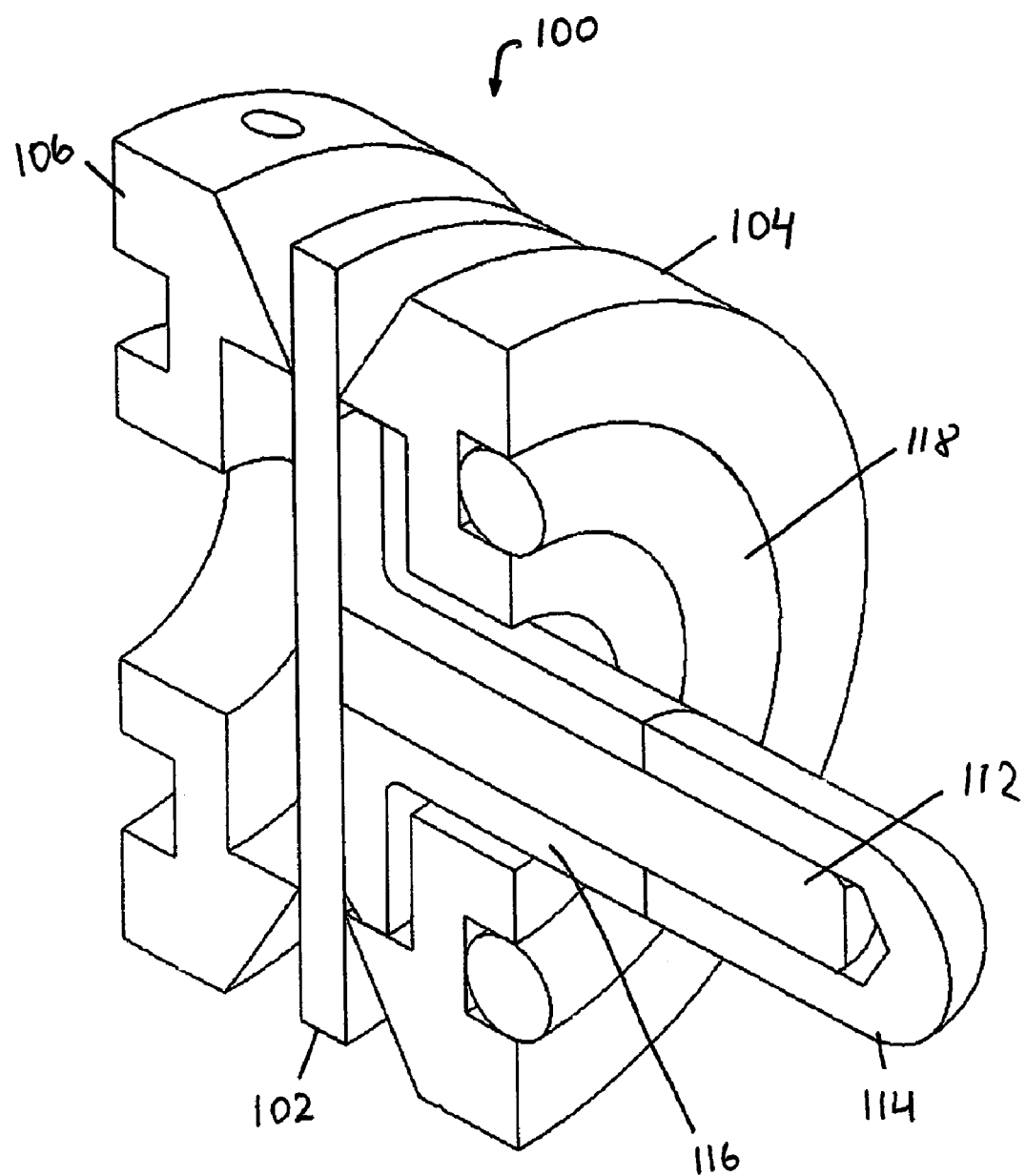
FIG. 2 shows a cross-sectional perspective representation of the transducer according to an embodiment of the present invention, FIGS. 3(a) and (b) shows schematic representations of probes for non-destructive testing according to embodiments of the present invention, FIGS. 4(a) and (b) shows schematic representations of probes for non-destructive testing according to further embodiments of the present invention.

Referring to FIGS. 1 and 2 a transducer of a low frequency acoustic probe for non-destructive testing according to an embodiment of the present invention is now described. The transducer 100 comprises a bending actuator which in this embodiment is provided in the form of a disc 102. The disc 102 has a contact area 102a and a vibration surface 102b that surrounds the contact area. The disc 102 is bimorph and comprises two layers of PZT material which are polarised in an opposite direction. The transducer 100 comprises two mode setting clamping members 104 and 106 which clamp the transducer disc 102. The mode setting clamping members are in this embodiment ring shaped and have clamping surfaces which contact the transducer disc 102 at narrow ring-like portions. Each mode setting clamping member 104 and 106 has a clamping surface on the apex of a tapered portion.

In this embodiment the thickness and diameter of the transducer disc 102 are derived from finite element computer model (FEM) calculations for optimal response of drive efficiency versus harmonic characteristics. The positions of the narrow ring-like clamping regions are selected so that the first natural bending mode of the transducer disc is unsuppressed by the clamping. This results in suppressing of at least some unwanted artificial resonances and expands the usable frequency range for non-destructive testing to higher frequencies such as up to 30, 40 or even 50 kHz.

It is to be appreciated that in alternative embodiments the mode setting clamping members may take any other suitable form. For example, they may not necessarily be ring-like and may not clamp the transducer disc 102 at a closed ring-like clamping area. Clamping may be effected at discrete regions, for example at points along a line on the transducer disc 102. In alternative embodiments the mode setting clamping members 104 and 106 may be arranged to suppress bending modes of any other order.

In this embodiment the mode setting clamping members 104 and 106 are composed of a suitable rigid metallic material and may also comprise a gold coating. The mode setting clamping members 104 and 106 provide electrical connections for the transducer disc 102. In this example the mode setting clamping members 104 and 106 have a diameter of 6-15 mm and a thickness of 0.3-1.0 mm.

The transducer comprises a spring loaded mechanism 110 that pushes the transducer housing 108 against a test structure with a predefined constant loading pressure. The transducer 100 further comprises an O-ring 118 composed of a rubber-like material which preloads the mode setting clamping member 104 and thereby facilitates clamping of the transducer disc 102 and ensures electrical contact.

In this embodiment a coupling pin 112 is rigidly connected to the transducer disc 102 and establishes via wear-pin 114 coupling between the transducer disc 102 and a surface of a test structure. In this embodiment the coupling pin 112 is composed of stainless steel but may alternatively be composed of any other suitable material. The coupling pin typically is a cylindrical pin having a diameter of 1-3 mm and a length of 5-20 mm.

The mode setting clamping members 104 and 106 have a precision fit in housing 108 which aligns the mode setting members 104 and 106.

Further, the transducer 100 comprises a stiffening element 116 which is positioned around a portion of the coupling pin 112 and at the transducer disc 102. The wear-pin 114 and stiffening element 116 are composed of a plastics material. The stiffening element 116 fits into a portion of the mode setting clamping member 104 in the same manner a piston fits into a cylinder which aligns the bending actuator 102 with pin 112 relative to the mode setting clamping members 104 and 106.

The transducer 100 may be used to generate an acoustic wave by applying an ac voltage to the mode setting clamping members 104 and 106 and thereby to the transducer disc 102. Alternatively the transducer 100 may be used to receive an acoustic wave, for example a return signal from a test structure. In this case the acoustic wave will generate a vibration of the transducer disc 102 which in turn generates a voltage at the mode setting clamping members 104 and 106. The voltage signal may then be analysed to qualify the test structure (electrical connections of the mode setting clamping members 104 and 106 are not shown).

Figure 3:
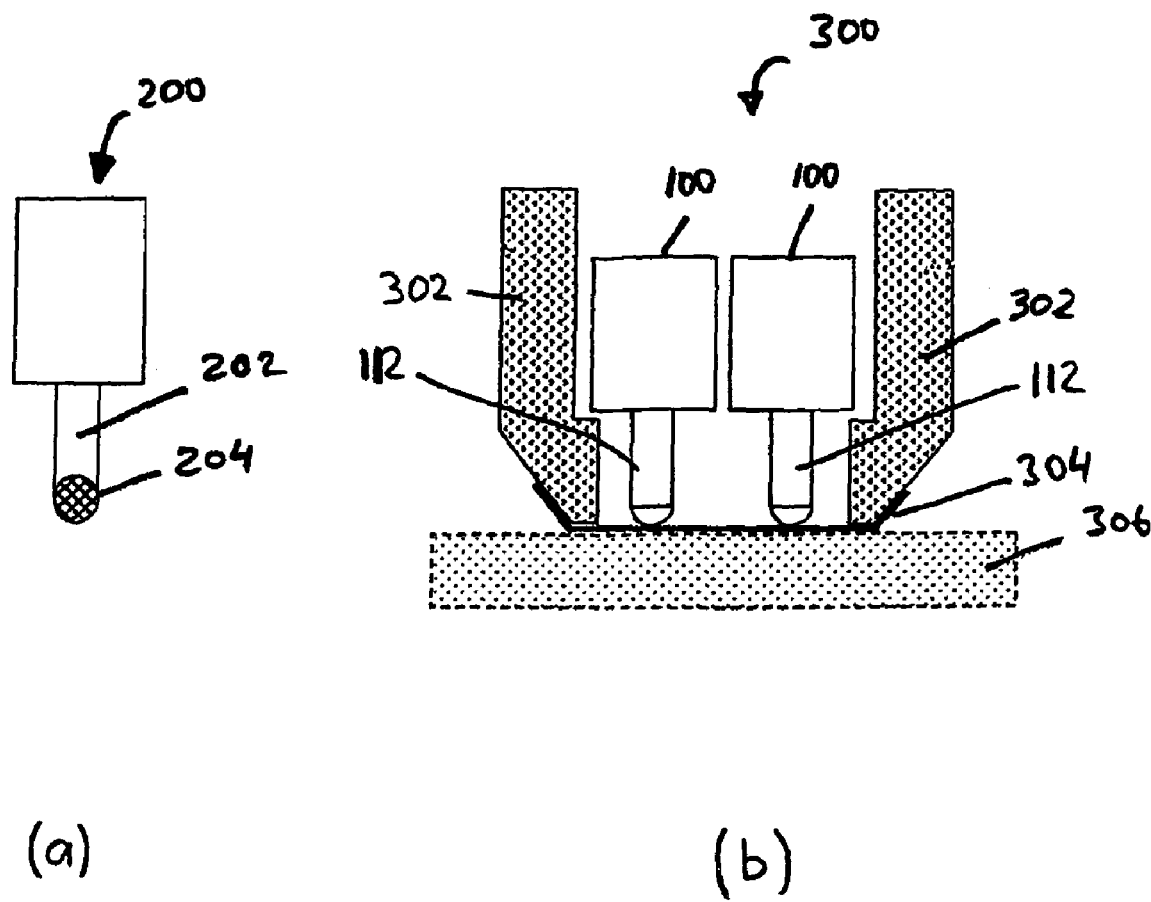

FIG. 3(a) shows a transducer 200 which is similar to the transducer 100 described above and comprises a pin 202. In this embodiment the pin 202 has a ball-bearing 204 at an end portion which reduces friction when the transducer 200 is moved over the surface of a test structure. FIG. 3(b) shows a probe 300 comprising two of the transducers 100 with contact pins 112. The transducers 100 are positioned in a housing 302 and the probe 300 also comprises a resilient film 304 positioned over an opening of the housing 302 in a manner such that the coupling pins 112 establish contact with a test structure 306 via the resilient film 304. The resilient film, which may be composed of a polymeric material, reduces friction when the probe 300 is moved over the surface of the test structure 306.

Figure 4:
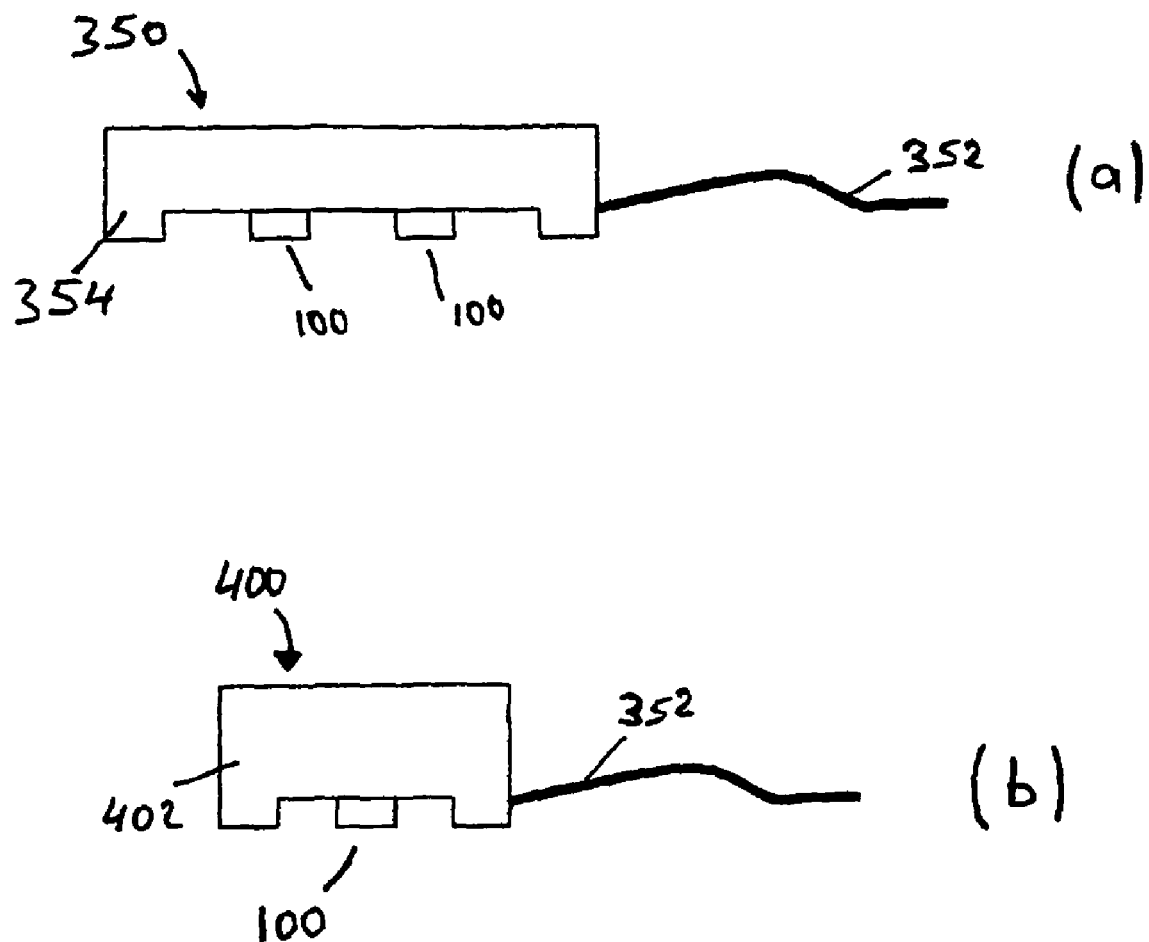

FIG. 4(a) shows a low frequency acoustic probe for non-destructive testing. The probe 350 comprises a housing and is arranged for connection to a computer for driving electronics via electrical leads 352. Further, the probe 350 comprises a housing 354 which comprises two of the above-described transducers 100. A first transducer 100 is arranged for generating an acoustic wave and a second transducer 100 is arranged for receiving a response signal from a test structure.

FIG. 4(b) shows a low frequency acoustic probe for non-destructive testing according to a further embodiment of the present invention. The probe 400 comprises electrical leads 352 for connection to a computer or driving electronics. Further, the probe 400 comprises a housing 402 which comprises the above-described transducer 100 and additional electronic components. In this embodiment the transducer 100 of the probe 400 is arranged for both generating an acoustic wave and receiving an acoustic return signal from a test structure. By measuring the impedance of the transducer 100 it is possible to derive the return signal and thereby characterise the test structure.

Figure 5:
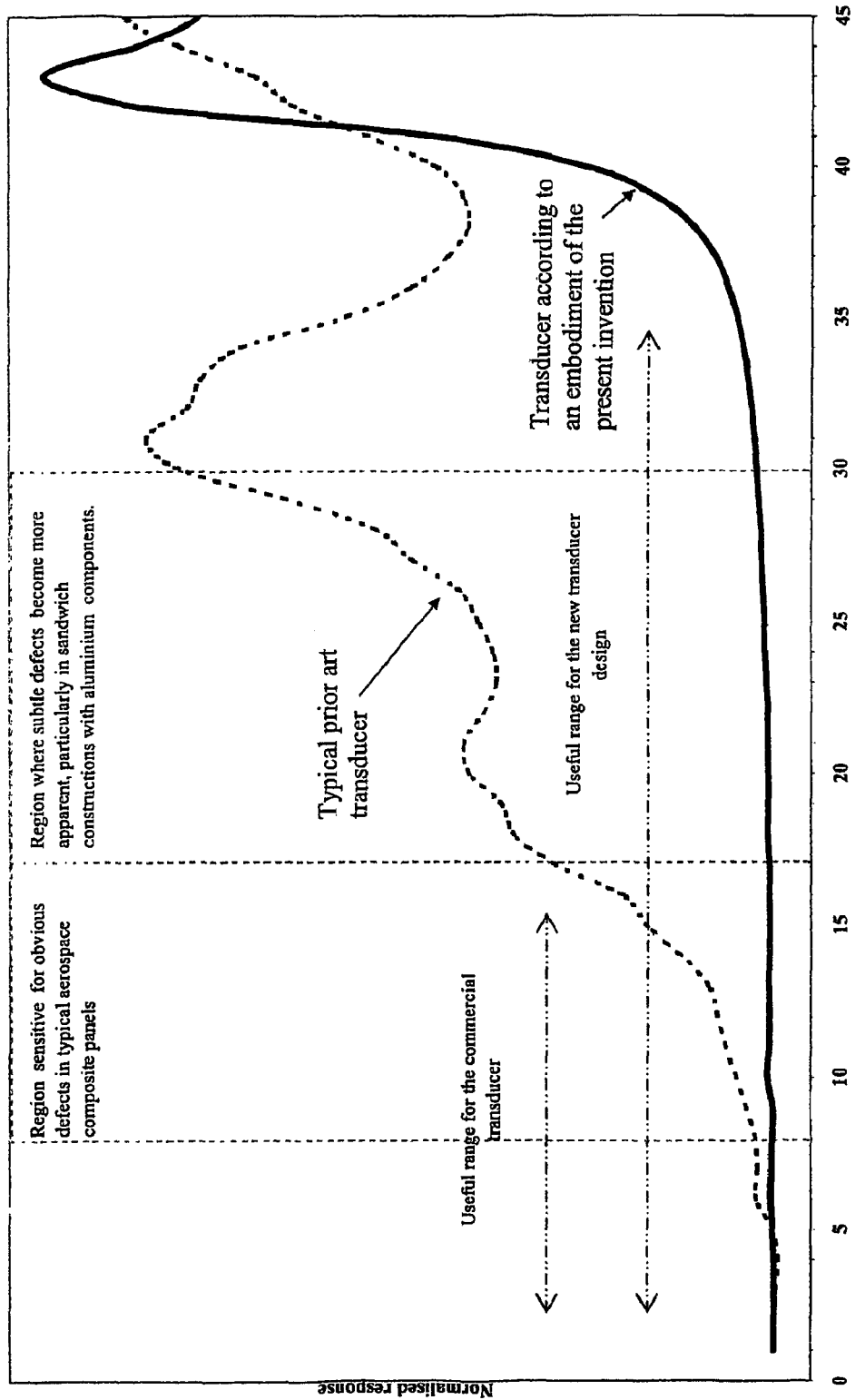
FIG. 5 shows plots of responses of transducers according to the present invention and according to the prior art.

FIG. 5 shows a response for both a conventional non-destructive testing probe according to the prior art, and a non-destructive testing probe according to an embodiment of the present invention. The conventional probe displays strong resonant enhancements at approximately 20 and 31 kHz that are not present on the probe according to an embodiment of the present invention, which is largely flat up to approximately 35 kHz. Consequently the useful range for probe according to an embodiment of the present invention is increased to approximately 35 kHz. In this embodiment the probe comprises a disc-shaped PZT bending actuator having a diameter of 8 mm and a thickness of 0.52 mm with a reinforced inner layer of brass. A solid plastic pin (diameter 2 mm, length 6 mm) is used with no stiffening element. The bending actuator is held between two mode setting clamping rings each having a rounded contact face and the diameter of the ring-shaped contact surface is 5.3 mm.

Although the invention has been described with reference to particular examples, it will be appreciated by those skilled in the art that the invention may be embodied in many other forms. For example, each transducer may comprise only one mode setting element which is bonded or otherwise rigidly connected at selected narrow portions to the bending actuator.

The invention claimed is:

1. A low frequency acoustic transducer for a probe for non-destructive testing of a test structure, the transducer being arranged for conversion between electrical energy and acoustic energy associated with an acoustic wave that propagated or will propagate through a portion of the test structure, and comprising:
   a bending actuator for generating an acoustic wave by generating a vibration from an electrical signal or for generating an electrical signal from a vibration generated by a received acoustic wave, the bending actuator having a vibration surface and a contact area surrounded by a portion of the vibration surface, and
   a mode setting member having a rigid portion which is in direct mechanical contact with the bending actuator at the contact area such that, within the contact area, an amplitude of the vibration is substantially suppressed, wherein the transducer comprises a coupling pin that is rigidly attached to the bending actuator.

2. The transducer as claimed in claim 1 wherein the mode setting member supports the bending actuator and the bending actuator is only supported by the mode setting member.

3. The transducer as claimed in claim 1 wherein the mode setting member is arranged so that a natural fundamental bending mode, which the bending actuator would also have without the mode setting member, is unsuppressed.

4. The transducer as claimed in claim 1 having a frequency within a range between 100 Hz and 50 kHz that is largely free of any resonances.

5. The transducer as claimed in claim 1 having a frequency within a range between 1 kHz and 40 kHz that is largely free of any resonances.

6. The transducer as claimed in claim 1 having a frequency within a range between 2 kHz and 28 kHz that is largely free of any resonances.

7. The transducer as claimed in claim 1 wherein the vibration surface includes opposite first and second side portions of the bending actuator and wherein the mode setting member comprises a first mode setting clamping member positioned at the first side portion of the bending actuator and a second mode setting clamping member positioned at the second side portion of the bending actuator so that the bending actuator is clamped between the mode setting members.

8. The transducer as claimed in claim 7 wherein the first and second mode setting clamping members are shaped to clamp the bending actuator at opposite positions along a closed line on the first and second sides of the bending actuator.

9. The transducer as claimed in claim 7 wherein the first and second mode setting clamping members each have a ring-like continuous clamping surface which clamp the bending actuator.

10. The transducer as claimed in claim 7 wherein the first and second mode setting clamping members are arranged for clamping at points or separated areas along the line.

11. The transducer as claimed in claim 7 wherein the mode setting clamping members have a ring-like clamping surface that has a tapered cross-sectional profile having a clamping edge.

12. The transducer as claimed in claim 7 wherein the clamping surface is circular and the bending actuator also has a circular disc-like shape.

13. The transducer as claimed in claim 7 wherein the first and the second mode setting clamping members are electrically conductive members and provide electrical connections for the bending actuator.

14. The transducer as claimed in claim 1 wherein coupling pin is positioned and shaped so that the coupling pin does not result in an additional bending or compressional mode associated with a frequency that is below that of a natural bending mode of the bending actuator.

15. The transducer as claimed in claim 1 wherein the transducer comprises a stiffening element at a bottom portion of the bending actuator and around the coupling pin.

16. The transducer as claimed in claim 15 wherein the stiffening element has a diameter which is between 0.25 and 0.9 of that of the bending actuator.

17. The transducer as claimed in claim 15 wherein the stiffening element is shaped and coupled to the mode setting member so that the stiffening element promotes self-alignment of the mode setting member and the bending actuator relative to each other.

18. The transducer as claimed in claim 10 wherein the stiffening element has a diameter which is between 0.25 and 0.9 of that of the bending actuator and wherein the diameter of the stiffening element is approximately the same as that of the ring-like contact area of the mode setting clamping members.

19. The transducer as claimed in claim 15 wherein the stiffening element and the coupling pin are integrally formed from the same material.

20. A low frequency acoustic transducer for a probe for non-destructive testing of a test structure, the transducer being arranged for conversion between electrical energy and acoustic energy associated with an acoustic wave that propagated or will propagate through a portion of the test structure, and comprising:
a bending actuator for generating an acoustic wave by generating a vibration from an electrical signal or for generating an electrical signal from a vibration generated by the received acoustic wave, the bending actuator having opposite first and second surfaces,
a first contact member contacting the first side portion of the bending actuator, and
a second contact member contacting the second side portion of the bending actuator,
wherein the first and second contact members clamp the bending actuator and provide electrical contacts for the bending actuator,
wherein the transducer comprises a coupling pin that is rigidly attached to the bending actuator.

21. A probe for non-destructive testing comprising the transducer as claimed in claim 1.

22. The probe as claimed in claim 21 wherein the transducer is one of at least two transducers.

23. The probe as claimed in claim 22 wherein at least one transducer of the probe is arranged for generating the acoustic wave and another transducer of the probe is arranged for receiving a return signal from the test structure.

24. The probe as claimed in claim 21 wherein the probe is arranged for generating the acoustic wave and receiving a return signal by the same transducer and wherein the probe is arranged for measurement of an electrical impedance of the transducer during testing of a test structure from which a response signal can be derived.

25. A method of generating an acoustic wave for non-destructive testing of a test structure, the method comprising:
applying an ac electrical signal to a bending actuator for generating a vibration, the bending actuator being rigidly attached to a coupling pin, the vibration generating an acoustic wave for propagation through a portion of the test structure, the bending actuator having a vibration surface and a contact area surrounded by a portion of the vibration surface, and
contacting the bending actuator by a rigid portion of a mode setting member at the contact area such that, at the contact area, an amplitude of the vibration is substantially suppressed.

26. The method as claimed in claim 25 wherein the step of contacting the bending actuator comprises clamping the bending actuator between mode setting clamping members at a ring-like area of the bending actuator.

27. The method as claimed in claim 25 comprising the additional step of controlling a resonance frequency of the bending actuator by applying a dc voltage or selected additional ac voltage across at least a portion of the bending actuator.

28. A method of receiving an acoustic wave for non-destructive testing of a test structure, the method comprising:
exposing a bending actuator to the acoustic wave received from the test structure whereby a vibration and an associated ac voltage is generated, the bending actuator having a vibration surface and a contact area surrounded by a portion of the vibration surface, and
contacting the bending actuator by a rigid portion of a mode setting member at the contact area such that, at the contact area, an amplitude of the vibration is substantially suppressed, the bending actuator being rigidly attached to a coupling pin.

29. The method of claim 28 wherein the step of contacting the vibration surface comprises clamping the bending actuator between mode setting clamping members at a ring-like area of the bending actuator.

* * * * *